United States Patent [19]

Shroot et al.

[11] Patent Number: 5,212,203

[45] Date of Patent: * May 18, 1993

[54] AROMATIC BENZAMIDO COMPOUNDS; THEIR PREPARATION AND THEIR USE IN HUMAN OR VETERINARY MEDICINE OR IN COSMETIC PREPARATIONS

[75] Inventors: Braham Shroot, Antibes; Jacques Eustache, Grasse; Jean-Michel Bernardon, Nice, all of France

[73] Assignee: Centre International de Recherches Dermatogologiques (C.I.R.D.), Valbonne, France

[ * ] Notice: The portion of the term of this patent subsequent to Feb. 23, 2007 has been disclaimed.

[21] Appl. No.: 483,625

[22] Filed: Feb. 23, 1990

Related U.S. Application Data

[63] Continuation of Ser. No. 5,727, Jan. 21, 1987, Pat. No. 4,927,928.

[30] Foreign Application Priority Data

Jan. 21, 1986 [LU]  Luxembourg ............. 86258

[51] Int. Cl.$^5$ ............................. A61K 31/165
[52] U.S. Cl. ................... 514/617; 514/622; 514/826; 514/859; 514/863; 514/912
[58] Field of Search .............. 514/617, 622, 863, 859, 514/826, 912; 548/528; 562/455

[56] References Cited

U.S. PATENT DOCUMENTS 4,927,928  5/1990  Shroot et al. ................. 548/528

FOREIGN PATENT DOCUMENTS 045990  4/1973  Japan .................... 562/455
127943  4/1973  Japan .................... 562/455

Primary Examiner—Frederick E. Waddell
Assistant Examiner—K. E. Weddington
Attorney, Agent, or Firm—Cushman, Darby & Cushman

[57] ABSTRACT

An aromatic benzamido compound having the formula

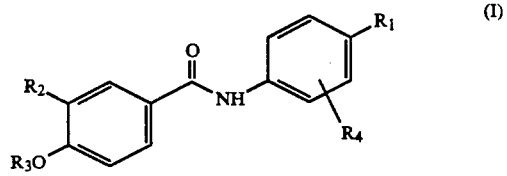

(I)

wherein $R_1$ represents —CH$_2$OH, —CHOHCH$_3$ or —COR$_5$, $R_5$ represents hydrogen, lower alkyl, —OR$_6$ or

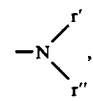

$R_6$ represents hydrogen, lower alkyl or mono- or polyhydroxyalkyl, r' and r" represent hydrogen, lower alkyl, mono or polyhydroxyalkyl, aryl or benzyl optionally substituted, the residue of an amino acid or aminated sugar or taken together form a heterocycle, $R_2$ represents an α,α'-disubstituted alkyl having 4–12 carbon atoms or mono or polycyclic cycloalkyl having 5–12 carbon atoms, the linking carbon of which is quaternary, $R_3$ represents hydrogen or alkyl having 1–10 carbon atoms, and $R_4$ represents hydrogen, lower alkyl or hydroxy, and the salts of this aromatic benzamido compound when $R_6$ represents hydrogen.

13 Claims, No Drawings

AROMATIC BENZAMIDO COMPOUNDS; THEIR PREPARATION AND THEIR USE IN HUMAN OR VETERINARY MEDICINE OR IN COSMETIC PREPARATIONS

This is a continuation of application Ser. No. 07/005,727, filed Jan. 21, 1987; U.S. Pat. No. 4,927,928.

The present invention relates to new aromatic benzamido derivatives, a process for their preparation and their use in human and veterinary medicine and in cosmetic compositions.

These new aromatic benzamido derivatives are usefully employed in the topical and systemic treatment of dermatologic ailments linked to a keratinization disorder (differentiation-proliferation) and dermatologic diseases, or others, having an inflammatory and/or immunoallergic component and in degenerative conjunctive tissue diseases, as well as an antitumoral activity. Besides, these derivatives can be used in the treatment of atrophies, be they cutaneous or respiratory, and in rheumatoid psoriasis.

The compounds of the present invention are also useful in the field of ophthalmology, principally in the treatment of corneopathies.

The aromatic benzamido derivatives in accordance with the present invention have the following formula

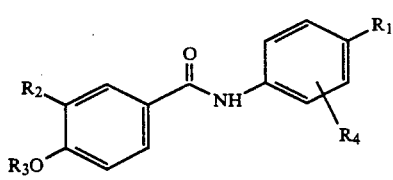

wherein $R_1$ represents —CH$_2$OH, —CHOHCH$_3$ or —COR$_5$,
$R_5$ represents hydrogen, lower alkyl, —OR$_6$ or

$R_6$ represents hydrogen, lower alkyl or mono- or polyhydroxy alkyl, r' and r" represent hydrogen, lower alkyl, mono or polyhydroxy alkyl, aryl or benzyl optionally substituted, the residue of an amino acid or an aminated sugar or, when taken together they form a heterocycle, $R_2$ represents an α,α'-disubstituted alkyl radical having 4–12 carbon atoms or a mono or polycyclic cycloalkyl radical having 5–12 carbon atoms wherein the linking carbon atom thereof is quaternary, $R_3$ represents hydrogen or alkyl having 1–10 carbon atoms, and $R_4$ represents hydrogen, lower alkyl or hydroxy, and the salts of said aromatic benzamido derivatives of formula I when $R_6$ represents hydrogen.

When the compounds of the present invention are provided in the form of salts, the salts are salts of an alkali metal or alkaline earth metal or even of zinc or an organic amine.

By lower alkyl radical is meant a radical having from 1 to 6 carbon atoms, principally methyl, ethyl, isopropyl, butyl and tert.butyl.

By monohydroxyalkyl radical is meant a radical having 2 or 3 carbon atoms, principally 2-hydroxyethyl, 2-hydroxypropyl or 3-hydroxypropyl.

By polyhydroxyalkyl is meant a radical containing from 3 to 6 carbon atoms and from 2 to 5 hydroxyl groups, such as 2,3-dihydroxypropyl, 2,3,4-trihydroxybutyl, 2,3,4,5-tetrahydroxypentyl or the residue of pentaerythritol.

By aryl radical is meant a phenyl radical optionally substituted by halogen, hydroxy or a nitro function.

By α,α'-disubstituted radical having 4 to 12 carbon atoms a tert.butyl radical, 1,1-dimethyl propyl, 1-methyl-1-ethyl propyl, 1-methyl-1-ethyl hexyl or 1,1-dimethyl decyl.

By mono or polycyclic cycloalkyl radical having 5 to 12 carbon atoms whose linking carbon atom is quaternary, is meant 1-methyl cyclohexyl or 1-adamantyl.

By the residue of an amino acid is meant a residue derived, for example, from lysine or glycine.

By residue of an aminated sugar is meant a residue derived for example from glucosamine, galactosamine or mannosamine.

When the radicals r' and r" together form a heterocycle, it is preferably piperidino, piperazino, morpholino, pyrrolidino or 4-(2-hydroxyethyl)-piperazino.

Representative aromatic benzamido derivatives of formula I, above, include in particular:

4-[3-(1-adamantyl)-4-methoxy benzamido] benzoic acid,
4-[3-(1-adamantyl)-4-methoxy benzamido] methyl benzoate,
N-[4-[3-(1-adamantyl)-4-methoxy benzamido]benzoyl] ethylamine,
4-[3-(1-adamantyl)-4-hydroxy benzamido] benzoic acid,
4-[3-(1-adamantyl)-4-hydroxy benzamido] methyl benzoate,
4-[3-(1-methylcyclohexyl)-4-methoxy benzamido] benzoic acid,
4-[3-(1-methylcyclohexyl)-4-methoxy benzamido] ethyl benzoate,
4-[3-(1-adamantyl)-4-decyolxy benzamido] benzoic acid,
4-[3-(1-adamantyl)-4-declyoxy benzamido] methyl benzoate,
4-[3-(1-adamantyl)-4-hexyloxy benzamido] benzoic acid,
4-[3-(1-adamantyl)-4-hexyloxy benzamido] methyl benzoate,
4-[3-(1,1-dimethyl decyl)-4-methoxy benzamido] benzoic acid,
4-[3-(1,1-dimethyl decyl)-4-methoxy benzamido] methyl benzoate,
4-(3-tert.butyl-4-methoxy benzamido) benzoic acid,
4-(3-tert.butyl-4-methoxy benzamido) methyl benzoate,
N-[4-[3-(1-adamantyl)-4-methoxy benzamido]-benzoyl] pyrrolidine,
N-[4-[3-(1-adamantyl)-4-methoxy benzamido]-benzoyl] piperidine,
N-[4-[3-(1-adamantyl)-4-methoxy benzamido] benzoyl] morpholine,
N-[4-[3-(1-adamantyl)-4-methoxy benzamido] benzoyl] tert. butylamine,
N-[4-[3-(1-adamantyl)-4-methoxy benzamido] benzoyl] ethylamine,
N-[4-[3-(1-adamantyl)-4-methoxy benzamido] benzoyl] aniline, N-[4-[3-(1-adamantyl)-4-methoxy benzamido] benzoyl] benzylamine, 4-[3-(1-adamantyl)-4-methoxy benzamido] 2-hydroxyethyl benzoate, N-(4-acteylphenyl)-3-(1-adamantyl)-4-methoxy benzamide, N-[4-(1-hydroxyethyl)phenyl]-3-(1-adamantyl)-4-methoxy benzamide, N-[4-[3-(1-adamantyl)-4-methoxy benzamido] benzoyl] 2-hydroxyethylamine, and 2-hydroxy-4-[3-(1-adamantyl)-4-methoxy benzamido] methyl benzoate.

The present invention also relates to a process for preparing the compounds of formula I in accordance with the following reaction scheme:

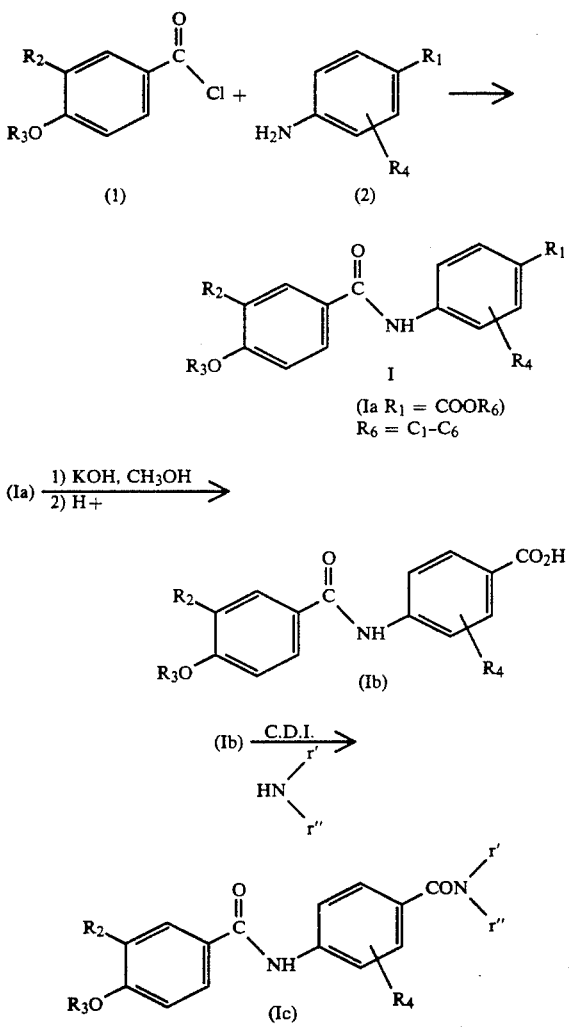

The principal step of this process comprises reacting in an anhydrous medium, in an organic solvent, which is preferably tetrahydrofuran, and in the presence of a tertiary amine, an activated form of a substituted benzoic acid, for example, an acid chloride (1) with an aminated compound of formula (2), the reaction being carried out at ambient temperature and with stirring.

Starting with ester (Ia) the corresponding acid (Ib) is produced by saponification, which acid can then be activited, for example, with the aid of N,N'-carbonyl diimidazole (CDI) or by conversion into the acid chloride, and then transformed into the amide of formula (Ic) by reaction with an amine of the formula

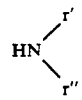

(r' and r" having the meanings given above).

When $R_6$ represents a monohydroxy or polyhydroxy radical it is preferable to prepare the acid (Ib) starting with the methyl ester (Ia) ($R_6 = $—$CH_3$) and then to esterify the resulting acid into the ester of a selected mono or polyhydric alcohol in accordance with known methods.

The compounds in which $R_1 = $—$CH_2OH$, and —$CHOHCH_3$ are obtained in a conventional manner by reduction, respectively, of the corresponding esters and ketones.

The present invention also relates to a medicine comprising the compounds of formula I, such as defined above.

These compounds exhibit excellent activity in the inhibition test of ornithine decarboxylase in nude rats after induction, by "tape stripping" (M. Boucher et al, DERMATOLOGIA, 169, No. 4, 1984). This test is recognized as a measure of the inhibitory activity of certain compounds on cellular proliferation phenomena.

These compounds are particularly appropriate for treating dermatologic ailments linked to a keratinization disorder (differentiation-proliferation) as well as dermatologic diseases, or others, having an inflammatory and/or immunoallergic component principally:

acnes vulgaris, comedons or polymorphs, solar senile acne and medicinal or professional acne, extensive and/or severe forms of psoriasis, and other keratinization disorders, and principally ichtyoses and ichtyosis-like conditions, Darier malady, palmo-plantar keratodermies, leucoplasies and leucoplasi-like states, lichen plan, and all malignant or benign dermatologic proliferations, severe or extensive.

The are also active in the treatment of tumors, of rheumatoid psoriasis, cutaneous or respiratory atopies as well as in certain ophthalmalogic problems relating to corneopathies.

The present invention also relates to a medicinal composition containing at least one compound of Formula I, such as defined above, or one of its salts.

The present invention thus relates to a new medicinal composition, intended for the treatment of the above mentioned disorders, comprising in a pharmaceutically acceptable vehicle or support at least one compound of Formula I and/or one of its salts.

The compounds according to the present invention exhibit good stability to light and oxygen.

The compounds according to the invention are generally administered at a daily dosage of about 0.01mg/kg to 5mg/kg of body weight.

As the vehicle or carrier for these compositions, any conventional vehicle can be employed, the active compound being found either in the dissolved state, or in the dispersed state, in said vehicle.

The administration of the compounds of the present invention can be effected enterally, parenterally, topically or ocularly.

When administered enterally, the medicines can be provided in the form of tablets, gelules, lozenges, syrups, suspensions, solutions, powders, granules or emulsions.

When administered parenterally, the medicinal compositions can be provided in the form of solutions or suspensions for perfusion or injection.

When administered topically, the pharmaceutical compositions, based on the compounds of the present invention, can be provided in the form of ointments, tinctures, creams, salves, powders, pads, impregnated tampons, solutions, lotions, gels, sprays, or suspensions.

These compositions for topical administration can be provided either under anhydrous form or in aqueous form according to clinical indications.

When administered ocularly, the composition is provided principally in the form of an eyewash.

These compositions contain at least one compound of Formula I, as defined above, or one of its salts, in an amount, preferably, between 0.0001 and 5 percent by weight based on the total weight of the composition.

The compounds of Formula I, according to the present invention, are also useful in the cosmetic field, in particular, in body and hair hygiene compositions and principally for the treatment of skin having acne tendencies, to improve the growth of hair, to combat hair loss, to combat against an oily appearance of the skin or hair, in the protection against the harmful effects of the sun or in the treatment of physiologically dry skin.

The present invention thus relates to a cosmetic composition containing, in a cosmetically acceptable vehicle, at least one compound of Formula I or one of its salts, this composition being provided principally in the form of a lotion, gel, soap or shampoo.

The concentration of the compound of Formula I in these cosmetic compositions is between 0.0001 and 0.1 percent by weight and, preferably, between 0.001 and 0.01 weight percent, based on the total weight of the composition.

The medicinal and cosmetic compositions according to the invention can contain inert or even pharmacodynamic or cosmetically active additives and principally: hydrating agents such as thiamorpholinone and its derivatives or urea; anti-seborrheic or anti-acne agents such as S-carboxy methylcysteine, S-benzyl methylcysteamine, their salts and their derivatives, tioxolone or benzoyl peroxide; antibiotics such as erythromycin and its esters, neomycin, tetracyclines or 4,5-polymethylene-3-isothiazolinones; agents promoting the growth of hair such as "Minoxidil" (2,4-diamino-6-piperidino-pyrimidine-3-oxide) and its derivatives, Diazoxide (7-chloro-3-methyl-1,2,4-benzothiadiazine-1,1-dioxide) and Phenytoin (5,5-diphenylimidazolidine-2,4 dione); steroidal and non-steroidal anti-inflammatory agents; carotenoids and principally, $\beta$-carotene; anti-psoriatic agents such as anthralin and its derivatives and 5,8,11,14-eicosatetraynoic and 5,8,11-eicosatriynoic acids, their esters and their amides.

The compositions according to the present invention can also contain flavor improving agents, preservatives, stabilizers, humidity regulating agents, pH regulating agents, osmotic pressure modifying agents, emulsifiers, UV-A and UV-B filters, anti-oxidants such as $\alpha$-tocopherol, butyl hydroxy anisole or butyl hydroxy toluene.

The following non-limiting examples illustrate the preparation of the active compounds of Formula I in accordance with the invention as well as compositions containing these compounds.

EXAMPLE 1

Preparation of 4-[3-(1-adamantyl)-4-methoxy benzamido] methyl benzoate (a) 3-(1-adamantyl)-4-methoxy benzoic acid In a round bottom flask there are introduced 5.4g (225 mmoles) of Mg and 30 ml of tetrahydrofuran. A solution of 48.3g (150 mmoles) of 2-adamantyl-4-bromo anisole, 6 ml (70 mmoles) of dibromoethane in 300 ml of tetrahydrofuran is then added. The reaction mixture is heated to reflux for two hours, cooled to $-70°$ C. and gaseous $CO_2$ is introduced for 1 hour. The temperature of the reaction mixture is left to return to 20° C., at which point it is poured into water, acidified to pH=1 with concentrated HCl and extracted with ethyl ether. The organic phase is decanted, dried over magnesium sulfate and evaporated. After recrystallization in ethyl acetate, 37 g of the expected product (86% yield) having a melting point of 238°–239° C. are obtained.

(b) 3-(1-adamantyl)-4-methoxy benzoyl chloride

In a round bottom flask, there are introduced 200 ml of thionyl chloride and there are then added, in small fractions, 35 g (122 mmoles) of the acid obtained in stage (a), above. The reaction mixture is heated to reflux until the emission of gases ceases. The reaction mixture is evaporated to dryness, taken up in 100 ml of anhydrous benzene and again evaporated to dryness, yielding 37 g of the expected product (100% yield) having a melting point of 153°–154° C.

(c) 4-[3-(1-adamantyl)-4-methoxy benzamido] methyl benzoate

In a round bottom flask, there are introduced 2.5 g (17 mmoles) of methyl p-amino benzoate, 50 ml of tetrahydrofuran and 2.6 ml (18.5 mmoles) of triethylamine. There are then slowly added 5.64 g (18.5 mmoles) of 3-adamantyl-4-methoxy benzoic acid chloride in 50 ml of tetrahydrofuran. The reaction mixture is stirred at ambient temperature for 2 hours, poured into water and extracted with methylene chloride. The organic phase is decanted, dried on magnesium sulfate and evaporated. After recrystallization in a 50:50 isopropyl ether-ethyl acetate mixture, 7.1 g of the expected product (92% yield) having a melting point of 179°–180° C. are obtained.

EXAMPLE 2

Preparation of 4-[3-(1-adamantyl)-4-methoxy benzamido] benzoic acid

In a round bottom flask, there are introduced 6 g (14 mmoles) of the ester obtained in Example 1 and 200 ml of 2 M methanolic NaOH. The reaction mixture is heated to reflux for 4 hours. It is then evaporated to dryness, taken up in water, acidified with HCl to pH=1, and extracted with ether. The organic phase is decanted, dried on magnesium sulfate and evaporated. After recrystyllization in ethyl acetate, 4g of the expected acid (69% yield) having a melting point of 286°–287° C. are obtained.

EXAMPLE 3

Preparation of 4-[3-(1-adamantyl)-4-hydroxy benzamido] methyl benzoate

(a) 3-(1-adamantyl)-4-tert.butyl dimethylsilyloxy benzoic acid

In a round bottom flask, there are introduced 1.18 g (48.8 mmoles) of magnesium and 20ml of THF. There are then slowly added 13.79 (32.5 mmoles) of tert.butyl dimethylsilic ether of 2-(1-adamantyl)-4-bromophenol, described in European application No. 86/400785.1, and the reaction mixture is heated at reflux for 2 hours. It is then cooled to −70° C. and a stream of $CO_2$ is passed therethrough for 1 hour. The temperature is permitted to return to 20° C., at which point the reaction mixture is poured into water, acidified with concentrated HCl to pH=1, and extracted with ethyl ether. The organic phase is decanted washed with water, dried on magnesium sulfate and the solvents evaporated. The residue is pulverized in 200 ml of isopropyl ether at reflux. After cooling, the precipitate is filtered, yielding 8.20 g (65% yield) of 3-(1-adamantyl)-4-tert.butyl dimethylsilyloxy benzoic acid which melts at 245°-246° C.

(b) 3-(1-adamantyl)-4-tert.butyldimethyl-silyloxy benzoic acid chloride 6.45 g (16.7 mmoles) of the acid obtained in 3(a), above, are suspended in 100 ml of $CH_2Cl_2$. There are then added 3.3 ml (16.7 mmoles) of dicyclohexylamine and the reaction mixture is stirred for 1 hour at 20° C. There ar then added 1.35 ml (18.4 mmoles) of thionyl chloride. The reaction mixture is stirred for 2 hours at ambient temperature, evaporated to dryness and taken up in 300 ml of ether. The salt formed is filtered and the ether phase is evaporated, yielding 6.9 g (100% yield) of 3-(1-adamantyl)-4-tert.butyldimethylsilyloxy benzoic acid chloride, in the form of a solid which is used, as is, in the following synthesis.

(c) 4-[3-(1-adamantyl)-4-tert.butyl dimethylsilyloxy benzamido]methyl benzoate In a round bottom flask, there are introduced 2.10 g (13.9 mmoles) of methyl p-amino benzoate, 2.10 ml (15.3 mmoles) of triethylamine and 50ml of THF. There are then slowly added 6.20g (15.3 mmoles) of 3-(1-adamantyl)-4-methoxybenzoyl chloride and the reaction mixture is stirred at ambient temperature for 4 hours.

The reaction mixture is poured into water, extracted with methylene chloride, dried on MgSO4 and the solvents are evaporated. The resulting solid is recrystallized in a 10:1 diisopropyl ether-ethyl acetate mixture to give 6.5g (91% yield) of the expected ester which melts at 183°-184° C.

(d) 4-[3-(1-adamantyl)-4-hydroxy benzamido] methyl benzoate

In a round bottom flask, there are introduced 6.40 g (12.3 mmoles) of the ester obtained in 3(c) above and 75 ml of THF. 13.5ml (13.5 mmoles) of tetrabutylammonium fluoride (1M in THF) are slowly added. The reaction mixture is stirred at ambient temperature for 2 hours, then poured into water and extracted with methylene chloride. The organic phase is decanted, dried on magnesium sulfate and the solvents are evaporated.

The resulting solid is pulverized in 200 ml of ethyl acetate at reflux, cooled and filtered, yielding 4.20 g (84% yield) of the methyl ester of 4-[3-(1-adamantyl)-4-hydroxy benzamido] benzoic acid which melts at 305°-306° C.

Example 4

Preparation of 4-[3-(1-adamantyl)-4-hydroxy benzamido]benzoic acid

A suspension of 3.3 g (8.1 mmoles) of the ester obtained in 3(d), above, in 100 ml of 2N methanolic NaOH is stirred for 12 hours at ambient temperature. The reaction mixture is evaporated to dryness, taken up in water and acidified to pH=0 with concentrated HCl. The resulting solid is filtered, washed with water and dried under a vacuum in the presence of phosphorous pentoxide ($P_2O_5$). The solid is then pulverized in 200 ml of ethyl acetate at reflux. The mixture is cooled to ambient temperature and the resulting precipitate is filtered, yielding 2.8 g (88% yield) of 4-[3-(1-adamantyl)-4-hydroxy benzamido]benzoic acid which melts at 348°-249° C.

EXAMPLE 5

Preparation of 4-[3-(1-methylcyclohexyl)-4-methoxybenzamido] ethyl benzoate

(a) 4-bromo-2-(1-methylcyclohexyl) phenol

A mixture of methylene cyclohexane (0.96 g, 10 mmoles), p-bromophenol (1.73 g, 10 mmoles) and acid resin (Dowex 50×12—150 mg) is heated at 80° C. for 16 hours. The residue is purified by silica gel chromatography (eluant: 50/50 mixture of $CH_2Cl_2$/hexane). On evaporation of the solvents 0.50 g (19% yield) of 4-bromo-2-(1-methylcyclohexyl) phenol in the form of a yellowish oil is obtained.

(b) 4-bromo-2-(1-methylcyclohexyl) anisole

The 4-bromo-2-(1-methylcyclohexyl) phenol (9.26 g, 34.4 mmoles) is dissolved in 50 ml of THF. The solution is cooled to 0° C. and there is added in small fractions sodium hydride (80% in oil, 1.14 g, 37.8 mmoles). The reaction mixture is stirred for 30 minutes at ambient temperature and 5.37 g (37.8 mmoles) of methyl iodide are slowly added. Stirring is continued for 16 hours at which point water (300 ml) is added and the reaction mixture is extracted with ether (3×300 ml). The organic phase is washed with a saturated sodium bicarbonate solution and then with a saturated sodium chloride solution. The reaction mixture is dried on MgSO4, filtered and the solvents are evaporated. The residue is purified by chromatography on a silica column, eluted by a 20/80 mixture of dichloromethane and hexane, yielding 9 g (92% yield) of 4-bromo-2-(1-methylcyclohexyl) anisole in the form of a colorless oil.

(c) 3-(1-methylcyclohexyl)-4-methoxy benzoic acid

The compound obtained in 5(b), above, (9.0 g, 31.8 mmoles) is dissolved in 50ml of dry THF. The resulting solution is slowly added to magnesium (850 mg, 35 mmoles) and an iodine crystal. The reaction mixture is heated to reflux after the addition of the first 5 milliliters of solution. Reflux is maintained for 15 minutes after the addition is terminated. The reaction mixture is then cooled to −40° C. and a stream of $CO_2$ is passed therethrough for one hour. The mixture is poured into 6N HCl, and extracted with ether (3×300ml). The organic phase is washed with water until neutral, dried on MgSO₄ and evaporated. The resulting residue is pulverized in hexane, filtered and dried, yielding 6.50 g (82% yield) of 3-(1-methylcyclohexyl)-4-methoxy benzoic acid which melts at 199° C.

(d) 3-(1-methylcyclohexyl)-4-methoxy benzoyl chloride

In a round bottom flask, there are introduced 4.96g (20 mmoles) of 3-(1-methylcyclohexyl)-4-methoxy benzoic acid, 75 ml of dichloromethane, and 4ml (20 mmoles) of dicyclohexylamine. The reaction mixture is stirred for 1 hour. To the resulting solution, there are added 1.45 ml (20 mmoles) of thionyl chloride (SOCl₂ and the mixture is stirred for 2 hours at ambient temperature. The reaction mixture is then evaporated to dryness and taken up in 200 ml of ether. The dicyclohexyl-ammonium chloride is filtered off and the solvent is evaporated, yielding 5.30 g (100% yield) of crude 3-(1-methylcyclohexyl)-4-methoxy benzoyl chloride which is used, as is, for the following synthesis:

(e) 4-[3-(1-methylcyclohexyl)-4-methoxy benzamido] ethyl benzoate

In a round bottom flask, there are introduced 3.3 g (20 mmoles) of ethyl p-aminobenzoate, 3.1 ml (20 mmoles) of triethylamine and 75 ml of THF. 5.3 g (20 mmoles) of the acid chloride obtained in 5(d), above, in 50 ml of THF are slowly added and the mixture is stirred at ambient temperature for 2 hours. The reaction mixture is poured into water and extracted with methylene chloride. The organic phase is decanted, dried on MgSO₄ and the solvents are evaporated, yielding 6.30 g (80% yield) of 4-[3-(1-methylcyclohexyl)-4-methoxy benzamido]ethyl benzoate in the form of an oil.

Example 6

Preparation of 4-[3-(1-methylcyclohexyl)-4-methoxybenzamido] benzoic acid

In a round bottom flask, there are introduced 5.20g (13.1 mmoles) of the ester obtained in 5(e), above, and 150 ml of 2N methanolic NaOH. The reaction mixture is stirred at ambient temperature for 24 hours, evaporated to dryness, taken up in water, acidified to pH=0 with concentrated HCl, extracted with ether, dried on MgSO₄ and evaporated. The residue is recrystallized in an 8/2 mixture of isopropyl ether and ethyl acetate, yielding 3.9 g (82% yield) of 4-[3-(1-methylcyclohexyl)-4-methoxybenzamido] benzoic acid which melts at 230°-231° C.

EXAMPLE 7

Preparation of 4-[3-(1-adamantyl)-4-decyloxy benzamido] methyl benzoate 2.00 g (5 mmoles) of the ester obtained in 3(d), above, are dissolved in 70 ml of dimethyl formamide (DMF) and added slowly to a suspension of sodium hydride (80% in oil, 150 mg, 5 mmoles) in 20 ml of DMF. The reaction mixture is stirred at ambient temperature until the emission of gases ceases. 1.1 ml (5 mmoles) of 1-iododecane are added and the reaction mixture is stirred for 4 hours at ambient temperature. The reaction mixture is poured into water and extracted with ether. The organic phase is decanted, washed with water, dried on MgSO₄ and the solvents evaporated. The residue is purified by chromatography on a silica column (eluant: CH₂Cl₂), yielding 2.5 g (92% yield) of 4-[3-( 1-adamantyl)-4-decyloxy benzamido] methyl benzoate which melts at 106°-107° C.

EXAMPLE 8

Preparation of 4-[3-(1-adamantyl)-4-decyloxy benzamido] benzoic acid

In a manner analogous to that of Example 4, 2.00 g (3.67 mmoles) of the ester obtained in Example 7, treated for 48 hours with 100 ml of 2N methanolic NaOH produces 1.8 g (95% yield) of 4-[3-( 1-adamantyl)-4-decyloxybenzamido] benzoic acid which melts at 247°-248° C.

EXAMPLE 9

Preparation of 4-[3-(1-adamantyl)-4-hexyloxy benzamido] methyl benzoate

In a manner analogous to that of Example 7, starting with 2.50 g (6.2 mmoles) of the ester obtained in Example 3(d), above, treated with 187 mg (6.2 mmoles) of sodium hydride (80% in oil) and 0.9 ml (6.2 mmoles) of 1-iodohexane, there are obtained 2.9 g (96% yield) of 4-[3-(1-adamantyl)-4-hexyloxy benzamido] methyl benzoate which melts at 154°-155° C.

EXAMPLE 10

Preparation of 4-[3-(1-adamantyl)-4-hexyloxy benzamido] benzoic acid

In a manner analogous to Example 8, starting with 2.27 g (4.6 mmoles) of the ester obtained in Example 9, there are obtained 2.10 g (96% yield) of 4-[3-(1-adamantyl)-4-hexyloxy benzamido] benzoic acid which melts at 256°-257° C.

EXAMPLE 11

Preparation of 4-[3-(1,1-dimethyldecyl)-4-methoxy benzamido] methyl benzoate (a) 4-bromo-2-(1,1-dimethyldecyl) phenol A mixture of p-bromophenol (25.85 g, 149 mmoles) and 2-methylundec-1-ene (25.15 g, 149 mmoles) is stirred at 110° C. for 48 hours in the presence of an acid resin (Dowex 50×12, 3 g). The resulting mixture is purified by chromatography on a silica column (eluant: 50/50 mixture of dichloromethane and hexane), yielding 25.04 g (49% yield) of 4-bromo-2-(1,1-dimethyldecyl) phenol in the form of a light yellow oil.

(b) 4-bromo-2-(1,1-dimethyldecyl) anisole

To a solution of the phenol obtained in Example 11(a), above, (24.88 g, 72.9 mmoles) in THF (200 ml), there are added, in small portions, 2.19 g (72.9 mmoles) of sodium hydride (80% in oil). Once the addition is completed, the reaction mixture is stirred for 1 hour at ambient temperature at which point methyl iodide (10.35 g, 72.9 mmoles) is slowly added. The reaction mixture is stirred for 2 hours at ambient temperature, the solvent is evaporated, water (300 ml) is added and the reaction mixture is extracted with ether (3×200 ml). The organic phase is washed with a saturated sodium chloride solution, dried on MgSO₄ and the solvents evaporated, yielding 22.2g (86% yield) of 4-bromo-2-(1,1-dimethyldecyl) anisole in the form of a yellow oil.

(c) 3-(1,1-dimethyldecyl)-4-methoxy benzoic acid

The 4-bromo-2-(1,1-dimethyldecyl) anisole (15.72 g, 44.2 mmoles) obtained in Example 11(a), above, is dissolved in THF (50 ml). This solution is slowly added to magnesium (1.18 g, 48.7 mmoles) and an iodine crystal, while being maintained at reflux by heating. Once the addition is complete, the reaction mixture is maintained at reflux for 30 minutes and then cooled to −40° C. 300 ml of THF are added and a stream of $CO_2$ is passed therethrough for 2 hours. The reaction mixture is then poured into a solution of HCl (4N, 300 ml) and the product is extracted with ether (3×300 ml). The organic phase is washed with water until neutral, dried on $MgSO_4$, and the solvents are evaporated. The residue is pulverized in isooctane to produce 7.25 g (51% yield) of 3-(1,1-dimethyldecyl)-4-methoxy benzoic acid which melts at 112° C.

(d) 3-(1,1-dimethyldecyl)-4-methoxy benzoyl chloride

The acid obtained in Example 11(c), above, (7.18 g, 22.4 mmoles) is suspended in 200 ml of dichloromethane. Dicyclohexylamine (40.6 g, 22.4 mmoles) is slowly added and the mixture is cooled to 0° C. Thionyl chloride (2.66 g, 22.4 mmoles) is added and the reaction mixture is stirred for 16 hours at ambient temperature. The precipitate which forms is filtered and the solvent evaporated, thus yielding, quantitatively, crude 3-(1,1-dimethyldecyl)-4-methoxybenzoyl chloride in the form of a white solid which is used, as is, for the following synthesis.

(e) 4-[3-(1,1-dimethyldecyl)-4-methoxybenzamido] methyl benzoate

All of the acid chloride obtained in Example 11(d), above, is dissolved in 50ml of THF. The resulting solution is added to a solution of methyl p-aminobenzoate (3.39g, 22.4 mmoles) and triethylamine (2.27 g, 22.4 mmoles) in THF (150ml). The reaction mixture is stirred for 1 hour at ambient temperature. The resulting precipitate is filtered and the solvent is evaporated. The product is purified by column chromatography (eluant: dichloromethane). The solvents are evaporated and the resulting solid is pulverized in hexane, filtered and dried, yielding 7.72 g (76% yield) of 4-[3-(1,1-dimethyldecyl)-4-methoxybenzamido] methyl benzoate which melts at 120° C.

EXAMPLE 12

Preparation of 4-[3-(1,1-dimethyldecyl)-4-methoxy benzamido] benzoic acid

The ester obtained in Example 11(e), above, (2.5 g, 5.51 moles) is mixed with 110ml of methanol. 11 ml of 5N NaOH are added and the reaction mixture is stirred for three days. The methanol is evaporated and 4N HCl (200 ml) is added. The product is extracted with dichloromethane (3×300 ml). The organic phase which is washed with a saturated sodium bicarbonate solution and then with sodium chloride, is dried over $MgSO_4$ and the solvent is evaporated. The resulting solid is pulverized in hexane, filtered and then dried, yielding 1.57 g (65% yield) of 4-[3-(1,1-dimethyldecyl)-4-methoxybenzamido] benzoic acid which melts at 177° C.

EXAMPLE 13

Preparation of 4-(3-tert.butyl-4-methoxy benzamido) methyl benzoate

Crude 3-(tert.butyl)-4-methoxy) benzoic acid chloride prepared from 10.14 g (50 mmoles) of 3-(tert.butyl)-4-methoxy benzoic acid described in French patent application 85.13747 (2.570.377), is dissolved in 60ml of THF. The solution is added slowly over a mixture of methyl 4-aminobenzoate (7.14 g, 47.2 mmoles) and triethylamine (4.78 g, 47.2 mmoles), in solution in THF (50 ml). The reaction mixture is stirred for 3 hours at ambient temperature. The precipitate that forms is filtered and the solvents are evaporated. 300 ml of water are added and the product is extracted with ether (3×200 ml).

The organic phase which is washed with a saturated sodium bicarbonate solution and then with sodium chloride is dried on $MgSO_4$, filtered and the solvents are evaporated. The resulting solid is recrystallized in hexane containing about 5% methanol, yielding 14.02 g (87% yield) of 4-(3-tert.butyl-4-methoxybenzamido) methyl benzoate.

EXAMPLE 14

Preparation 4- 3-tert.butyl-4-methoxy benzamido) benzoic acid

In a manner analogous to that of Example 4, starting with 5 g (14.65 mmoles) of the ester obtained in Example 13, above, 4.27 g (89%) yield of 4-(3-tert.butyl-4-methoxybenzamido) benzoic acid, which melts at 250° C., are obtained.

Example 15

Preparation of N-[4-[3-(1-adamantyl)-4-methoxybenzamido]-benzoyl] pyrrolidine 1.7 g (9 mmoles) of N-p-aminobenzoyl pyrrolidine and 1 g (10 mmoles) of triethylamine are dissolved in 30 ml of dichloromethane. With stirring, 2.8 g (9 mmoles) of 3-(1-adamantyl)-4-methoxybenzoyl chloride dissolved in 60 ml of dichloromethane are added. The reaction mixture is stirred for 16 hours, at which point water is added and the reaction mixture is extracted with dichloromethane. The extract is washed with water, extracted with methylene chloride and dried on $MgSO_4$. The solvents are evaporated and the residue (yellow foam) is crystallized in ethyl acetate to give 3.0 g (73% yield) of N-[4-[3-(1-adamantyl)-4-methoxy benzamido]-benzoyl] pyrrolidine which melts at 239°–242° C.

EXAMPLE 16

Preparation of N-[4-[3-(1-adamantyl)-4-methoxybenzamido]-benzoyl] piperidine

In a manner analogous to that of Example 15, above, starting with 0.7 g (3.6 mmoles) of N-[4-amino benzoyl] piperidine, 1.0 g (63% yield) of N-[4-[3-(1-adamantyl)-4-methoxybenzamido]-benzoyl] piperidine is obtained.

EXAMPLE 17

Preparation of N-[4-[3-(1-adamantyl)-4-methoxy benzamido] benzoyl] morpholine

In a manner analogous to that of Example 15, above, starting with 3.0 g (15 mmoles) of N-[4-aminobenzoyl]-morpholine, methoxy benzamido]benzoyl] morpholine which melts at 238°–241° C. are obtained.

EXAMPLE 18

Preparation of N-[4[3-(1-adamantyl)-b 4methoxy benzamido] benzoyl] tert. butylamine Starting with 1.0g (5 mmoles) of N-tert.butyl-4-aminobenzamide, 1.5 g (63% yield) of N-[4-[3-(1- adamantyl)-4-methoxy benzamido] benzoyl] tert. butylamine which melts at 270°–273° C. are obtained.

EXAMPLE 19

Preparation of N-[4-[3-(1-adamantyl)-4-methoxy benzamido]benzoyl]ethylamine (a) 4-[3-(1-adamantyl)-4-methoxy benzamido] benzoic acid chloride 2.0 g (5 mmoles) of 4-[3-(1-adamantyl)-4-methoxy benzamido] benzoic acid are dissolved in 60 ml of THF. 1.1 g (6 mmoles of dicyclohexylamine are slowly added. A white precipitate is immediately formed. The reaction mixture is then cooled to 0° C. and 0.7 g (6 mmoles) of thionyl chloride is slowly added. The reaction mixture is stirred for 3 hours at ambient temperature. The solid that forms is filtered and then the filtrate is evaporated. The resulting residue is used, as is, in the following synthesis.

(b) N-[4-[3-(1-adamantyl)-4-methoxy benzamido] benzoyl] ethylamine

The crude acid chloride obtained in Example 19(a), above, is dissolved in 80 ml of THF. There is then slowly added a solution of ethylamine (0.5 g, 11 mmoles) in dry THF (20 ml). The reaction mixture is stirred for 16 hours at ambient temperature, filtered and the filtrate is evaporated. The reddish residue thus obtained is recrystallized in ethanol to give 0.5 g (24% yield) of N-[4-[3-(1-adamantyl)-4-methoxy benzamido] benzoyl] ethylamine which melts at 274°–277° C.

EXAMPLE 20

N-4-[3-(1-adamantyl)-4-methoxy benzamido] benzoyl] aniline

This compound is obtained in accordance with the same procedures as those described in Example 19. 0.7 g (30% yield) of the expected product which melts at 265°–268° C. is obtained.

EXAMPLE 21

Preparation of N-[4-[3-(1-adamantyl)-4-methoxy benzamido] benzoyl] benzylamine

This compound is obtained in accordance with the same procedures as those described in Example 19. 0.2 g (9% yield) of the expected product which melts at 279°–280° C. is obtained.

EXAMPLE 22

Preparation of 4-[3-(1-adamantyl)-4-methoxy benzamido] 2-hydroxy ethyl benzoate

The crude acid chloride obtained in Example 19(a), above, starting with 2 g of 4-[3-(1-adamantyl)-4-methoxy benzamido] benzoic acid is dissolved in a solution of ethylene glycol (1.4 g, 22 mmoles) and pyridine (0.8 g, 10 mmoles) in dry THF (20 ml). The reaction mixture is stirred for 16 hours at ambient temperature and is then filtered. The filtrate is evaporated to dryness to give a yellowish residue that is purified by column chromatography by using as the eluant a 1/1 mixture of dichloromethane and ethyl acetate. The solvents are evaporated, yielding 1.2g (55% yield) of the expected ester which melts at 201°–203° C.

EXAMPLE 23

Preparation of N-(4-acetyl phenyl)-3-(1-adamantyl)-4-methoxy benzamide

A solution of 5.7 g of 3-(1-adamantyl)-4-methoxy benzoyl chloride, obtained in Example 1(b), above, in dichloromethane (60 ml) is slowly added to a mixture of 4-aminoacetophenone (2.6 g, 19 mmoles) and triethylamine (2.1 g, 21 mmoles) in dichloromethane (30 ml). The mixture is stirred for 16 hours then poured into water and extracted with dichloromethane. The organic phase is recovered, washed with water, dried on magnesium sulfate, then evaporated. The resulting residue is recrystallized in ethylacetate, yielding 3.0 g (39% yield) of N-(4-acetyl phenyl)-3-(1-adamantyl)-4-methoxybenzamide in the form of white crystals having a melting point of 200°–201° C.

EXAMPLE 24

Preparation of N-[4-(1-hydroxy ethyl) phenyl]-3-(1-adamantyl)-4-methoxy benzamide The amide obtained in Example 23, above, (0.9 g, 2 mmoles) is dissolved in methanol (25ml) and treated with 0.12 g (3 mmoles) of sodium borohydride. The mixture is stirred at ambient temperature for 2 days, poured into water and extracted with ether. The extracts are dried on magnesium sulfate, then the solvent is evaporated. The resulting residue is recrystallized in ethyl acetate to give N[4-[1-hydroxyethyl)phenyl]-3-(1-adamantyl)-4-methoxy benzamide (0.5 g, 66% yield) having a melting point of 207°–209° C.

EXAMPLE 25

Preparation of N-[4-[3-(1-adamantyl)-4-methoxy benzamido] benzoyl] 2-hydroxyethylamine In a manner analogous to that of Example 19, above, the N-[4-[3-(1-adamantyl)-4methoxy benzamido] benzoyl] 2-hydroxyethylamine is obtained (1.1 g, 50% yield) which melts at 265°–268° C. (crystallized in an ethanol-ether mixture).

EXAMPLE 26

Preparation of 2-hydroxy-4-[3-(1-adamantyl)-4-methoxy benzamido] methyl benzoate (a) methyl 4-amino-2-tert.butyl dimethylsilyloxy benzoate 2.0 g (12 mmoles) of methyl 4-amino-2-hydroxy benzoate are dissolved in 30 ml of dimethylformamide (DMF) containing 2.8 g (28 mmoles) of triethylamine, and 70 mg (0.6 mmoles) of 4-N,N-dimthylamino pyridine. A solution of tert.butyl dimethylsilyl chloride (4.2 g, 28 mmoles) in 40 ml of DMF is slowly added. The reaction mixture is stirred for 2 days at ambient temperature and is then heated at 100° C. for 8 hours. The DMF is evaporated under a vacuum; water is added; and the reaction mixture is extracted with ether. The organic phase is recovered, dried and the solvent evaporated, yielding crude methyl 4-amino-2-tert.butyl dimethylsilyoxy benzoate which is used, as is, in the following synthesis.

(b) 2-tert.butyl dimethylsilyloxy-4-[3-(1-adamantyl)-4-methoxy benzamido]methyl benzoate The crude methyl 4-amino-2-tert.butyl dimethylsilyloxy benzoate of Example 26(a) above, (3.0 g, 10 mmoles) is dissolved in 20 ml of dry THF containing 1.1 g (10 mmoles) of triethylamine. A solution of 4-methoxy-3-(1-adamantyl) benzoyl chloride in 80 ml of dry THF is slowly added and the reaction mixture is stirred for 16 hours at 20° C. The reaction mixture is then evaporated to dryness, taken up in 100 ml of dichloromethane, washed with water, dried on MgSO$_4$ and evaporated to dryness. The resulting residue is recrystallized in an ethanol/ethylether mixture, yielding 2.7 g (48% yield) of 2-tert.butyl dimethylsilyloxy -4-[3-(1-adamantyl)-4-methoxy benzamido] methyl benzoate which melts at 225°–227° C.

(c) 2-hydroxy-4-[3-(1-adamantyl)-4-methoxy benzamido] methyl benzoate 2.7 g (5 mmoles) of the ester obtained in Example 26(b), above, are dissolved in 80 ml of THF. A 1 M solution of tetrabutyl ammonium fluoride in THF (6 ml) is added and the reaction mixture is stirred for 16 hours at 20° C. (the formation of a white precipitate is observed). The reaction mixture is evaporated to dryness, water is added and the reaction mixture is extracted with ether (3×100 ml). The extract is dried on MgSO$_4$ and evaporated to dryness (2.0 g), 95% yield); the residue is crystallized by the addition of a small amount of ether, thus yielding 2-hydroxy-4-[3-(1-adamantyl)-4-methoxy benzamido] methyl benzoate (1.6 g, 76% yield which melts at 207°–209° C.

EXAMPLES OF COMPOSITIONS

A. Orally Administrable Compositions

| Example (a) - 0.2 g tablet | |
|---|---|
| 4-[3-(1-adamantyl)-4-methoxy benzamido]methyl benzoate | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

| Example (b) - Drinkable suspension in 5 ml ampoules | |
|---|---|
| 4-[3-(1-adamantyl)-4-methoxy benzamido] benzoic acid | 0.001 g |
| Glycerine | 0.500 g |
| Sorbitol, 70% | 0.500 g |
| Sodium saccharinate | 0.010 g |
| Methyl parahydroxybenzoate | 0.040 g |
| Flavoring, sufficient amount | |
| Purified water, sufficient amount for | 5 ml |

B. Topically Administrable Compositions

| Example (a) - Ointment | |
|---|---|
| 4-[3-(1-adamantyl)-4-methoxy benzamido] benzoic acid | 0.020 g |
| Isopropyl myristate | 81.700 g |
| Fluid petrolatum oil | 9.100 g |
| Silica, sold under the trade designation "Aerosil 200" by Degussa | 9.180 g |

| Example (b) - Anhydrous hydrophobic ointment | |
|---|---|
| 4-[3-(1,1-dimethyldecyl)-4-methoxy benzamido] benzoic acid | 0.10 g |
| White petrolatum | 49.95 g |
| Triglycerides of capric and caprylic acids sold under the trade designation "Miglyol 812" by Dynamit Nobel | 49.95 g |

This ointment is obtained by mixing the petrolatum and "Miglyol 812" at 70° C. The active component is then introduced into the mixture by very carefully dispersing it with an ultrasonic bath by heating to 40°–50° C. The resulting ointment is then cooled with stirring.

In this Example, the active component (0.10 g) can be replaced by 0.5 g of 4-[3-(1-adamantyl)-4-hexyloxybenzamido] benzoic acid.

| Example (c) - Lotion | |
|---|---|
| 4-[3-(1-methylcyclohexyl)-4-methoxy benzamido] benzoic acid | 0.01 g |
| Absolute ethanol | 30.00 g |
| Polyethylene glycol (400) | 69.99 g |

This lotion is obtained by mixing the polyethylene glycol (400) and ethanol. The active component is introduced and dissolved therein in an ultrasonic bath.

| Example (d) - Oil-in-water anionic emulsion | |
|---|---|
| Sodium lauryl sulfate | 0.784 g |
| 1,2-propanediol | 1.570 g |
| White petrolatum | 19.502 g |
| Cetyl alcohol | 19.504 g |
| Methyl parahydroxy benzoate | 0.076 g |
| Propyl parahydroxy benzoate | 0.074 g |
| Sterile water, sufficient amount for | 100.00 g |

This emulsion is obtained by preparing the following A and B mixtures:

Mixture A

Sodium lauryl sulfate
1,2-propanediol
Methyl parahydroxy benzoate
Sterile water

After having dissolved the methyl parahydroxy benzoate with ultrasonic stirring, the mixture is heated to 70° C.

Mixture B

White petrolatum
Cetyl alcohol
Propyl parahydroxy benzoate

After having dissolved the propyl parahydroxy benzoate with ultrasonic stirring, the mixture is also heated to 75° C.

The emulsion is then formed by pouring Mixture A into Mixture B. After cooling to ambient temperature, the active component is introduced and the mixture is carefully stirred to thoroughly homogenize it. After packaging the emulsion, it is passed to a triclinder.

C. Cosmetic Compositions

| Example (a) - Non-oily fluid cream | |
|---|---|
| 4-[3-(1-adamantyl)-4-hexyloxy benzamido] methyl benzoate | 1.00 g |
| Palmito stearate of ethylene glycol and polyoxyethylenated glycol | 20.00 g |
| Saturated glycerides of poly oxyethylenated and glycolized $C_{10}$–$C_{18}$ | 3.00 g |

-continued

| Example (a) - Non-oily fluid cream | |
| --- | --- |
| Fluid petrolatum oil | 3.00 g |
| Preservatives | 0.05 g |
| Water, sufficient amount for | 100.00 g |

This cream is obtained by heating to 70° C. a mixture of the palmito stearate of ethylene glycol and polyoxyethylenated glycol, the saturated glycerides of polyoxyethylenated and glycolized $C_{10}$–$C_{18}$ and the petrolatum oil. The active component is then introduced and carefully dispersed therein. Water and the preservatives, also at a temperature of 70° C., are then poured into the above oily phase and stirring is continued until the temperature returns to ambient temperature and an emulsion is obtained.

In this Example, the active component can be replaced by the same amount of the morpholide of 4-[3-(1-adamantyl)-4-methoxy benzamido] benzoic acid.

| Example (b) - Cream with slightly oily consistency | |
| --- | --- |
| 4-(3-tert.butyl-4-methoxy benzamido) benzoic acid | 1.00 g |
| Mixture of mono and diglycerides of palmitic and stearic acids | 15.00 g |
| Sorbitan monostearate | 4.00 g |
| Sorbitan monostearate polyoxyethylenated with 20 moles of ethylene oxide | 1.20 g |
| Fluid petrolatum oil | 10.00 g |
| Preservatives | 0.04 g |
| Water, sufficient amount for | 100.00 g |

This cream is obtained in accordance with the same procedures as those described above.

In this Example, the active component can be replaced by the same amount of N-[4-[3-(1-adamantyl)-4-methoxy benzamido] benzoyl] ethylamine.

| Example (c) - Sun protection oil | |
| --- | --- |
| 4-[3-(1-adamantyl)-4-decyloxy benzamido] methyl benzoate | 0.50 g |
| 2-octyl dodecanol | 42.00 g |
| Triglycerides of capric and caprylic acids | 40.00 g |
| Mixture of the esters of capric ard caprylic acids with saturated fatty $C_{12}$–$C_{18}$ alcohols | 17.50 g |
| Example (d) - Alcoholic lotion for the scalp | |
| 4-(3-tert.butyl-4-methoxybenzamido benzoic acid | 0.80 g |
| Ethanol, 95% | 83.00 g |
| Water, Sufficient amount for | 100.00 g |
| Example (e) - 2 stage shampoo to be mixed at the time of use | |
| (i) - Treating stage | |
| 4-[3-(1-adamantyl)-4-decyloxy benzamido] methyl benzoate | 0.50 g |
| 2-octyl dodecanol | 50.00 g |
| Triglycerides of capric and caprylic acids | 49.50 g |
| (ii) - Washing stage | |
| Sodium lauryl ether sulfate | 50.00 g |
| Glycerol cocoate polyoxyethylenated with 7 moles of ethylene oxide | 5.00 g |
| Preservatives | 0.05 g |
| Water, sufficient amount for | 100.00 g |

At the moment of use, 10 g of the treating stage composition is mixed with 90 g of the washing stage composition.

What is claimed is:

1. A pharmaceutical composition comprising in a vehicle suitable for enteral, parenteral, topical or ocular administration, at least one aromatic benzamido compound having the formula

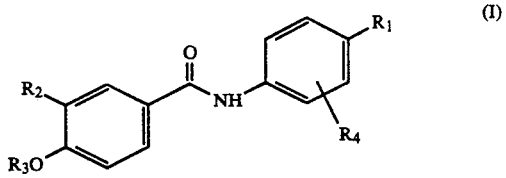

wherein
$R_1$ represents —$CH_2OH$, —$CHOHCH_3$ or —$COR_5$,
$R_5$ represents hydrogen, lower alkyl, $OR_6$ or

$R_6$ represents hydrogen, lower alkyl or mono- or polyhydroxyalkyl,
r' and r" represent hydrogen, lower alkyl, mono- or polyhydroxy alkyl, aryl or benzyl optionally substituted, the residue of an amino acid or aminated sugar or when taken together form a heterocycle,
$R_2$ represents an $\alpha,\alpha'$-disubstituted alkyl radical having 4–12 carbon atoms or mono or polycyclic cycloalkyl having 5–12 carbon atoms wherein the linking carbon is quaternary,
$R_3$ represents hydrogen or alkyl having 1–10 carbon atoms, and
$R_4$ represents hydrogen, lower alkyl or hydroxy, and the salts of said aromatic benzamido compound of Formula I when $R_6$ represents hydrogen.

2. The composition of claim 1 wherein said vehicle is suitable for topical application, said composition containing from 0.0001 to about 5 percent by weight of said compound based on the total weight of said composition.

3. A cosmetic composition for body and hair hygiene comprising in a cosmetically acceptable vehicle at least one aromatic benzamido compound having the formula

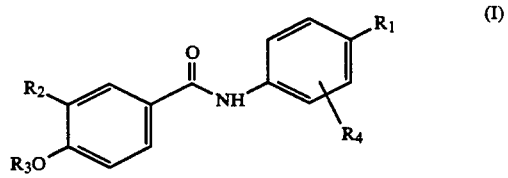

wherein
$R_1$ represents —$CH_2OH$, —$CHOHCH_3$ or —$COR_5$,
$R_5$ represents hydrogen, lower alkyl, $OR_6$ or

$R_6$ represents hydrogen, lower alkyl or mono- or polyhydroxyalkyl, r' and r" represent hydrogen, lower alkyl, mono- or polyhydroxy alkyl, aryl or benzyl optionally substituted, the residue of an amino acid or aminated sugar or when taken together form a heterocycle, $R_2$ represents an α,α'-disubstituted alkyl radical having 4-12 carbon atoms or mono or polycyclic cycloalkyl having 5-12 carbon atoms wherein the linking carbon is quaternary, $R_3$ represents hydrogen or alkyl having 1-10 carbon atoms, and $R_4$ represents hydrogen, lower alkyl or hydroxy, and the salts of said aromatic benzamido compound of Formula I when $R_6$ represents hydrogen.

4. The cosmetic composition of claim 3 wherein said compound is present in an amount ranging from 0.0001 to 0.1 percent by weight based on the total weight of said composition.

5. The cosmetic composition of claim 3 wherein said compound is present in an amount ranging from 0.001 to 0.01 percent by weight based on the total weight of said composition.

6. A composition comprising in an appropriate vehicle, an aromatic benzamido compound having the formula

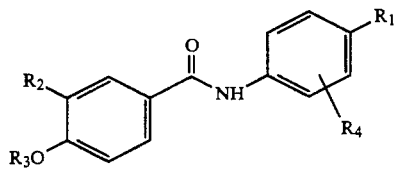

wherein $R_1$ represents —CH$_2$OH, —CHOHCH$_3$ or —COR$_5$, $R_5$ represents hydrogen, lower alkyl, OR$_6$ or

$R_6$ represents hydrogen, lower alkyl or mono- or polyhydroxyalkyl, r' and 4" represent hydrogen, lower alkyl, mono- or polyhydroxy alkyl, aryl or benzyl optionally substituted, the residue of an amino acid or aminated sugar or when taken together form a heterocycle, $R_2$ represents an α,α'-disubstituted alkyl radical having 4-12 carbon atoms or mono or polycyclic cycloalkyl having 5-12 carbon atoms wherein the linking carbon is quaternary, $R_3$ represents hydrogen or alkyl having 1-10 carbon atoms, and $R_4$ represents hydrogen, lower alkyl or hydroxy, and the salts of said aromatic benzamido compound of Formula I when $R_6$ represents hydrogen.

7. A pharmaceutical composition comprising in a vehicle suitable for enteral, parenteral, topical or ocular administration, at least one aromatic benzamido compound having the formula

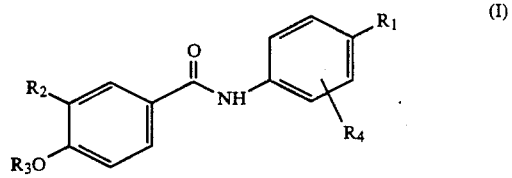

wherein $R_1$ represents —COR$_5$ wherein $R_5$ represents —OR$_6$ wherein $R_6$ represents hydrogen, lower alkyl or mono- or polyhydroxyalkyl, $R_2$ represents 1-adamantyl, $R_3$ represents alkyl having 1-10 carbon atoms, $R_4$ represents hydrogen, lower alkyl or hydroxy, and the pharmaceutically acceptable salts of said aromatic benzamido compound of formula I when $R_6$ represents hydrogen.

8. The pharmaceutical composition of claim 7 wherein said aromatic benzamido compound is selected from the group consisting of 4-[3-(1-adamantyl)-4-methoxy benzamido] benzoic acid, 4-[3-(1-adamantyl)-4-methoxy benzamido] methyl benzoate, N-[4-[3-(1-adamantyl)-4-methoxy benzamido] benzoyl) ethylamine, 4-[3-(1-adamantyl)-4hydroxy benzamido] benzoic acid, 4-[3-(1-adamantyl)-4-hydroxy benzamido] methyl benzoate, 4-[3-(1-methylcyclohexyl)-4-methoxy benzamido]-benzoic acid, 4-[3(1-methylcyclohexyl)-4-methoxy benzamido] ethyl benzoate, 4-[3-(1-adamantyl)-4-decyloxy benzamido]benzoic acid, 4-[3-(1-adamantyl)-4-decyloxy benzamido] methyl benzoate, 4-[3-(1-adamantyl)-4-hexyloxy benzamido] benzoic acid, 4-[3-(1-adamantyl)-4-hexyloxy benzamido] methyl benzoate, 4-[3-(1,1-dimethyl decyl)-4-methoxy benzamido] benzoic acid, 4-[3-(1,1-dimethyl decyl)-4-methoxy benzamido] methyl benzoate, 4-(3-tert. butyl-4methoxy benzamido) benzoic acid, 4-(3-tert. butyl-4-methoxy benzamido) methyl benzoate, N-[4-[3-(1-adamantyl)-4-methoxy benzamido] benzoyl] pyrrolidine, N-[4-[3-(1-adamantyl)-4-methoxy benzamido] benzoyl] piperidine, N-[4-[3-(1-adamantyl)-4-methoxy benzamido] benzoyl] morpholine, N-[4-[3-(1-adamantyl)-4-methoxy benzamido] benzoyl[ tert. butylamine, N-[4-[3-(1-adamantyl)-4-methoxy benzamido] benzoyl] ethylamine, N-[4-[3-(1-adamantyl)-4 -methoxy benzamido] benzoyl] anioline, N-[4-[3-(1-adamantyl)-4-methoxy benzamido] benzoyl ] benzylamine, 4-[3-(1-adamantyl)-4-methoxy benzamido] 2-hydroxyethyl benzoate, N-(4-acetylphenyl)-3(1-adamantyl)-4-methoxy benzamide, N-[4-(1-hydroxyethyl) phenyl]-3-(1-adamantyl)-4-methoxy benzamide, N-[4-[3-(1-adamantyl)-4-methoxy benzamido] benzoyl] 2-hydroxyethylamine and 2-hydroxy-4[3-(1-adamantyl)-4-methoxy benzamido]-methyl benzoate.

9. A cosmetic composition for body and hair hygiene comprising in a cosmetically acceptable vehicle at least one aromatic benzamido compound having the formula

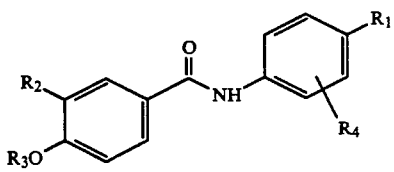

(I)

wherein $R_1$ represents —$COR_5$ wherein $R_5$ represents —$OR_6$ wherein $R_6$ represents hydrogen, lower alkyl or mono- or polyhydroxyalkyl, $R_2$ represents 1-adamantyl, $R_3$ represents alkyl having 1-10 carbon atoms, $R_4$ represents hydrogen, lower alkyl or hydroxy, and the cosmetically acceptable salts of said aromatic benzamido compound of formula I when $R_6$ represents hydrogen.

10. The cosmetic composition of claim 9 wherein said aromatic benzamido compound is selected from the group consisting of 4-[3-(1-adamantyl)-4-methoxy benzamido] benzoic acid, 4-[3-(1-adamantyl)-4-methoxy benzamido] methyl benzoate, N-[4-[3-(1-adamantyl)-4-methoxy benzamido] benzoyl] ethylamine, 4-[3-(1-adamantyl)-4-hydroxy benzamido] benzoic acid, 4-[3-(1-adamantyl)-4-hydroxy benzamido] methyl benzoate, 4-[3-(1-methylcyclohexyl)-4-methoxy benzamido]-benzoic acid, 4[3-(1-methylcyclohexyl-4-methoxy benzamido] ethyl benzoate, 4-[3-(1-adamantyl)-4-decyloxy benzamido]benzoic acid, 4-[3-(1-adamantyl)-4-decycloxy benamido] methyl benzoate, 4-[3-(1-adamantyl)-4-hexyloxy benzamido] benzoic acid, 4-[3-(1-adamantyl)-4-hexyloxy benzamido] methyl benzoate, 4-[3-(1,1-dimethyl decyl)-4-methoxy benzamido] benzoic acid, 4-[3-(1,1-dimethyl decyl)-4-methoxy benzamido] methyl benzoate, 4-(3-tert. butyl-4-methoxy benzamido) benzoic acid, 4-(3-tert. butyl-4methoxy benzamido) methyl benzoate, N-[4-[3-(1-adamantyl)-4-methoxy benzamido] benzoyl] pyrrolidine, N-[4-[3-(1-adamantyl)-4-methoxy benzamido] benzoyl] piperidine, N-[4-[3-(1-adamantyl)-4-methoxy benzamido] benzoyl] morpholine, N-[4-[3-(1-adamantyl)-4-methoxy benzamido] benzoyl] tert.butylamine N-[4-[3-(1-adamantyl)-4-methoxy benzamido] benzoyl] ethylamine, N-[4-[3-(1-adamantyl)-4-methoxy benzamido] benzoyl] aniline, N-[4-[3-(1-adamantyl)-4-methoxy benzamido] benzoyl] benzylamine, 4-[3-(1-adamantyl)-4-methoxy benzamido] 2-hydroxyethyl benzoate, N-(4-acetylphenyl)-3-(1-adamantyl)-4-methoxy benzamide, N-[4-(1-hydroxyethyl) phenyl]-3-(1-adamantyl)-4-methoxy benzamide, N-[4-[3(1-adamantyl)-4-methoxy benzamido] benzoyl] 2-hydroxyethylamine and 2hydroxy-4-[3-(1-adamantyl)-4-methoxy benzamido]-methyl benzoate.

11. A composition comprising in an appropriate vehicle, an aromatic benzamido compound having the formula

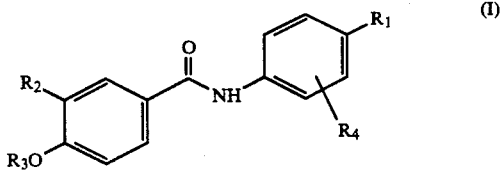

(I)

wherein $R_1$ represents —$COR_5$ wherein $R_5$ represents —$OR_6$ wherein $R_6$ represents hydrogen, lower alkyl or mono- or polyhydroxyalkyl, $R_2$ represents 1-adamantyl, $R_3$ represents alkyl having 1-10 carbon atoms, $R_4$ represents hydrogen, lower alkyl or hydroxy, and the salts of said aromatic benzamido compound of formula I when $R_6$ represents hydrogen.

12. A method for the treatment of a disorder selected from (i) a dermatologic ailment linked to a keratinization disorder, (ii) a dermatologic disease having an inflammatory component, (iii) a dermatologic disease having an immunoallergic component, (iv) rheumatoid psoriasis, (v) cutaneous atopy, (vi) respiratory atopy, (vii) an ophthalmologic disorder relating to corneopathies and (viii) malignant or benign dermatologic proliferations, said method comprising enterally, parenterally, topically or ocularly administering to a person suffering from said disorder the composition of claim 1 in an amount effective to treat said disorder.

13. A method for the treatment of a disorder selected from (i) a dermatologic disease ailment linked to a keratinization disorder, (ii) a dermatologic disease having an inflammatory component, (iii) a dermatologic disease having an immunoallergic component, (iv) rheumatoid psoriasis,
(v) cutaneous atophy,
(vi) respiratory atophy,
(vii) anophthalmologic disorder concerning corneopathies, and
(viii) malignant or benign dermatologic proliferations, said method comprising enterally, parenterally, topically or ocularly administering to a person suffering from said disorder the composition of claim 1 at a daily dosage of about 0.01 mg/kg to 5 mg/kg of body weight.

* * * * *